(12) United States Patent
Knuth et al.

(10) Patent No.: US 7,115,729 B2
(45) Date of Patent: Oct. 3, 2006

(54) ISOLATED NUCLEIC ACID MOLECULES WHICH ENCODE PEPTIDES WHICH BIND TO MHC CLASS II MOLECULES, SUCH AS HLA-DR53

(75) Inventors: Alexander Knuth, Frankfurt am Main (DE); Elke Jäger, Frankfurt am Main (DE); Yao-tseng Chen, New York, NY (US); Matthew Scanlan, New York, NY (US); Ali Gure, New York, NY (US); Gerd Ritter, New York, NY (US); Lloyd J. Old, New York, NY (US); Jan W. Drijfhout, Leiden (NL)

(73) Assignees: Cornell Research Foundation, Ithaca, NY (US); Ludwig Institute for Cancer Research, New York, NY (US); Memorial Sloan Kettering Cancer Center, New York, NY (US)

( * ) Notice: Subject to any disclaimer, the term of this patent is extended or adjusted under 35 U.S.C. 154(b) by 204 days.

(21) Appl. No.: 10/751,088

(22) Filed: Jan. 2, 2004

(65) Prior Publication Data

US 2004/0158044 A1    Aug. 12, 2004

Related U.S. Application Data

(60) Division of application No. 09/165,546, filed on Oct. 2, 1998, now Pat. No. 6,723,832, which is a continuation-in-part of application No. 09/062,422, filed on Apr. 17, 1998, now Pat. No. 6,252,052, which is a continuation-in-part of application No. 08/937,263, filed on Sep. 15, 1997, now Pat. No. 6,274,145, which is a continuation-in-part of application No. 08/725,182, filed on Oct. 3, 1996, now Pat. No. 5,804,381.

(51) Int. Cl.
| | | |
|---|---|---|
| *C12N 15/09* | (2006.01) | |
| *C12N 15/63* | (2006.01) | |
| *C12N 5/02* | (2006.01) | |
| *C07H 21/04* | (2006.01) | |

(52) U.S. Cl. .................... 536/23.5; 536/23.1; 435/325; 435/320.1

(58) Field of Classification Search ............... 536/23.1, 536/23.5, 24.1; 435/325, 320.1, 810
See application file for complete search history.

(56) References Cited

U.S. PATENT DOCUMENTS 5,804,381 A * 9/1998 Chen et al. .................... 435/6

OTHER PUBLICATIONS

Bodey, B et al. Anticancer Research [2000] 20:2665-2676.*
Marchand, M et al. Int. J. Cancer [1999] 20:219-230.*
Marchand, M et al. Exp. Opin. Biol. Ther. [2001] 1(3):497-510.*

* cited by examiner

*Primary Examiner*—Christina Chan
*Assistant Examiner*—F. Pierre VanderVegt
(74) *Attorney, Agent, or Firm*—Fulbright & Jaworski LLP

(57) ABSTRACT

The invention relates to peptides which bind to MHC Class I and to MHC Class II molecules. These peptides are useful in different therapeutic and diagnostic contexts.

8 Claims, 3 Drawing Sheets

FIG. 3

```
                ATCCTCGTGGGCCCTGACCTTCTCTCTGAGAGCCGGGCAGAGGCTCCGGAGC
              Myr     Myr     (P)
    M   Q   A   E   G   R   G   T   G   G   S   T   G   D   A   D   G   P   G   G
    CATGCAGGCCGAAGGCCGGGGCACAGGGGGTTCGACGGGCGATGCTGATGGCCCAGGAGG

P   G   I   P   D   G   P   G   G   N   A   G   G   P   G   E   A   G   A   T
    CCCTGGCATTCCTGATGGCCCAGGGGGCAATGCTGGCGGCCCAGGAGAGGCGGGTGCCAC

G   G   R   G   P   R   G   A   G   A   A   R   A   S   G   P   G   G   G   A
    GGGCGGCAGAGGTCCCCGGGGCGCAGGGGCAGCAAGGGCCTCGGGGCCGGGAGGAGGCGC

P   R   G   P   H   G   G   A   A   S   G   L   N   G   C   C   R   C   G   A
    CCCGCGGGGTCCGCATGGCGGCGCGGCTTCAGGGCTGAATGGATGCTGCAGATGCGGGGC
                                                                       (P)
    R   G   P   E   S   R   L   L   E   F   Y   L   A   M   P   F   A   T   P   M
    CAGGGGGCCGGAGAGCCGCCTGCTTGAGTTCTACCTCGCCATGCCTTTCGCGACACCCAT

E   A   E   L   A   R   R   S   L   A   Q   D   A   P   P   L   P   V   P   G
    GGAAGCAGAGCTGGCCCGCAGGAGCCTGGCCCAGGATGCCCCACCGCTTCCCGTGCCAGG
                                          (P)                  (P)
    V   L   L   K   E   F   T   V   S   G   N   I   L   T   I   R   L   T   A   A
    GGTGCTTCTGAAGGAGTTCACTGTGTCCGGCAACATACTGACTATCCGACTGACTGCTGC

D   H   R   Q   L   Q   L   S   I   S   S   C   L   Q   Q   L   S   L   L   M
    AGACCACCGCCAACTGCAGCTCTCCATCAGCTCCTGTCTCCAGCAGCTTTCCCTGTTGAT

W   I   T   Q   C   F   L   P   V   F   L   A   Q   P   P   S   G   Q   R   R
    GTGGATCACGCAGTGCTTTCTGCCCGTGTTTTTGGCTCAGCCTCCCTCAGGGCAGAGGCG

CTÅAGCCCAGCCTGGCGCCCCTTCCTAGGTCATGCCTCCTCCCCTAGGGAATGGTCCCAG
    CACGAGTGGCCAGTTCATTGTGGGGCCTGATTGTTTGTCGCTGGAGGAGGACGGCTTAC
    ATGTTTGTTTCTGTAGAAAATAAAACTGAGCTACGAAAAA
```

ISOLATED NUCLEIC ACID MOLECULES WHICH ENCODE PEPTIDES WHICH BIND TO MHC CLASS II MOLECULES, SUCH AS HLA-DR53

RELATED APPLICATION

This application is a divisional of Ser. No. 09/165,546, filed on Oct. 2, 1998, now U.S. Pat. No. 6,723,832 which is a continuation-in-part of Ser. No. 09/062,422, filed on Apr. 17, 1998, now U.S. Pat. No. 6,252,052, which is a continuation-in-part of Ser. No. 08/937,263, filed on Sep. 15, 1997, now U.S. Pat. No. 6,274,145, which is a continuation-in-part of Ser. No. 08/725,182, filed on Oct. 3, 1996, now U.S. Pat. No. 5,804,381. All patents are incorporated by reference.

FIELD OF THE INVENTION

This invention relates to HLA binding peptides derived from an antigen associated with cancer. These peptides bind to Class I and to Class II MHC molecules.

BACKGROUND AND PRIOR ART

It is fairly well established that many pathological conditions, such as infections, cancer, autoimmune disorders, etc., are characterized by the inappropriate expression of certain molecules. These molecules thus serve as "markers" for a particular pathological or abnormal condition. Apart from their use as diagnostic "targets", i.e., materials to be identified to diagnose these abnormal conditions, the molecules serve as reagents which can be used to generate diagnostic and/or therapeutic agents. A by no means limiting example of this is the use of cancer markers to produce antibodies specific to a particular marker. Yet another non-limiting example is the use of a peptide which complexes with an MHC molecule, to generate cytolytic T cells against abnormal cells.

Preparation of such materials, of course, presupposes a source of the reagents used to generate these. Purification from cells is one laborious, far from sure method of doing so. Another preferred method is the isolation of nucleic acid molecules which encode a particular marker, followed by the use of the isolated encoding molecule to express the desired molecule.

To date, two strategies have been employed for the detection of such antigens, in e.g., human tumors. These will be referred to as the genetic approach and the biochemical approach. The genetic approach is exemplified by, e.g., dePlaen et al., Proc. Natl. Sci. USA 85: 2275 (1988), incorporated by reference. In this approach, several hundred pools of plasmids of a cDNA library obtained from a tumor are transfected into recipient cells, such as COS cells, or into antigen-negative variants of tumor cell lines which are tested for the expression of the specific antigen. The biochemical approach, exemplified by, e.g., O. Mandelboim, et al., Nature 369: 69 (1994) incorporated by reference, is based on acidic elution of peptides which have bound to MHC-class I molecules of tumor cells, followed by reversed-phase high performance liquid chromagraphy (HPLC). Antigenic peptides are identified after they bind to empty MHC-class I molecules of mutant cell lines, defective in antigen processing, and induce specific reactions with cytotoxic T-lymphocytes. These reactions include induction of CTL proliferation, TNF release, and lysis of target cells, measurable in an MTT assay, or a $^{51}$Cr release assay.

These two approaches to the molecular definition of antigens have the following disadvantages: first, they are enormously cumbersome, time-consuming and expensive; and second, they depend on the establishment of cytotoxic T cell lines (CTLs) with predefined specificity.

The problems inherent to the two known approaches for the identification and molecular definition of antigens is best demonstrated by the fact that both methods have, so far, succeeded in defining only very few new antigens in human tumors. See, e.g., van der Bruggen et al., Science 254: 1643–1647 (1991); Brichard et al., J. Exp. Med. 178: 489–495 (1993); Coulie, et al., J. Exp. Med. 180: 35–42 (1994); Kawakami, et al., Proc. Natl. Acad. Sci. USA 91: 3515–3519 (1994).

Further, the methodologies described rely on the availability of established, permanent cell lines of the cancer type under consideration. It is very difficult to establish cell lines from certain cancer types, as is shown by, e.g., Oettgen, et al., Immunol. Allerg. Clin. North. Am. 10: 607–637 (1990). It is also known that some epithelial cell type cancers are poorly susceptible to CTLs in vitro, precluding routine analysis. These problems have stimulated the art to develop additional methodologies for identifying cancer associated antigens;

One key methodology is described by Sahin, et al., Proc. Natl. Acad. Sci. USA 92: 11810–11913 (1995), incorporated by reference. Also, see U.S. Pat. No. 5,698,396, and patent application Ser. No. 08/479,328 filed Jan. 3, 1996. All three of these references are incorporated by reference. To summarize, the method involves the expression of cDNA libraries in a prokaryotic host. (The libraries are secured from a tumor sample). The expressed libraries are then immunoscreened with absorbed and diluted sera, in order to detect those antigens which elicit high titer humoral responses. This methodology is known as the SEREX method ("Serological identification of antigens by Recombinant Expression Cloning"). The methodology has been employed to confirm expression of previously identified tumor associated antigens, as well as to detect new ones. See the above referenced patent applications and Sahin, et al., supra, as well as Crew, et al., EMBO J 144: 2333–2340 (1995).

The SEREX methodology has been applied to esophageal cancer samples, and an antigen has now been identified, and its encoding nucleic acid molecule isolated and cloned. This is the subject of several patent applications, some of which are incorporated by reference. The antigen and truncated forms have been found to be reactive with antibodies in the serum of cancer patients. It has also been found that peptides derived form this molecule bind with MHC molecules, provoking both cytolytic T cell and helper T cell responses. These features of the invention are seen in the disclosure which follows.

BRIEF DESCRIPTION OF THE FIGURES

FIG. 3 shows potential sites for modification of the deduced amino acid sequence of NY-ESO-1 (the amino acid sequence is encoded by the nucleotide sequence of SEQ ID NO: 1, and is set forth therein).

DETAILED DESCRIPTION OF PREFERRED EMBODIMENTS

EXAMPLE 1

Figure 1:
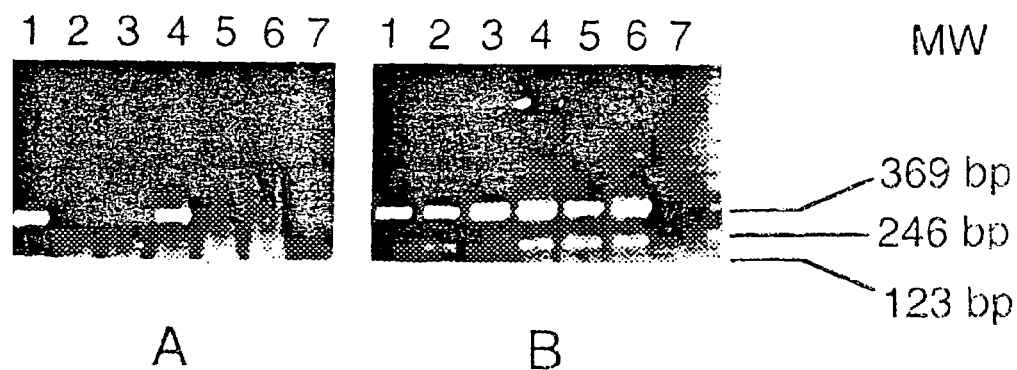
FIG. 1 shows the expression pattern of RNA for the NY-ESO-1 antigen, in various tissue types.
Figure 2:
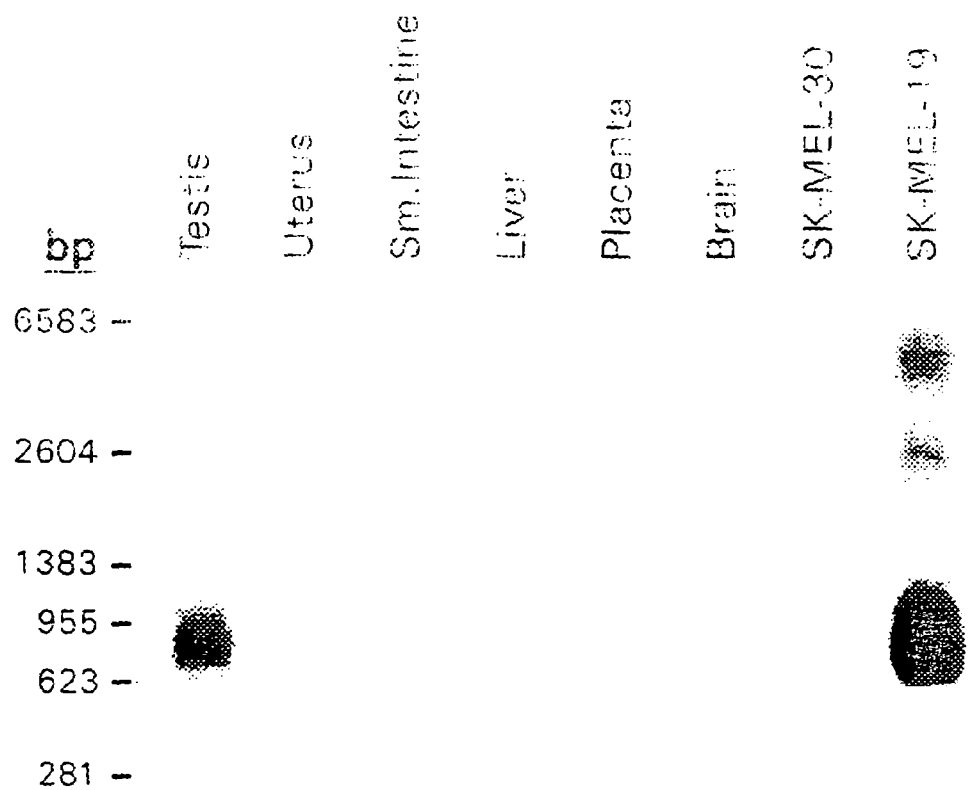
FIG. 2 shows Northern Blot analysis of NY-ESO-1 mRNA, which was found in testis and cell line SK-MEL-19, but not in various other cell and tissue samples.
Figure 4:
FIG. 4 is a hydrophilicity plot of NY-ESO-1, showing hydrophilic domains in the amino terminus and a long, hydrophobic stretch close to the carboxyl end.

Total RNA was extracted from a snap frozen specimen of well to moderately differentiated squamous cell cancer of the esophagus, using well known methods. See, e.g., Chomzynski, J. Analyt. Biochem. 162: 156–159 (1987), for one such method. This RNA was used to prepare a cDNA library which was then transfected into λZAP phage vectors, in accordance with the manufacturer's instructions. The λZAP library was then transfected into E. coli, yielding $1.6 \times 10^6$ primary isolates.

The SEREX methodology of Sahin, et al., Proc. Natl. Acad. Sci. USA 92: 11810–11813 (1995), incorporated by reference, was then used. In brief, autologous serum was stripped of antibodies against molecules which are endogenous to E. coli by combining the serum with lysates of E. coli transfected with phage λZAP which did not contain the cDNA clones from the esophageal cancer cells.

The depleted serum was then diluted, and mixed with nitrocellulose membranes containing phage plaques. The plaques were incubated overnight, at room temperature. Washing followed, and then the filters were incubated with alkaline phosphatase conjugated goat anti human FCγ secondary antibodies, and reactive phage plaques were visualized by incubating with 5-bromo-4-chloro-indolyl phosphate and nitroblue tetrazolium. A total of 13 positive clones were found.

EXAMPLE 2

Following identification, the reactive clones were subcloned to monoclonality via dilution cloning and testing with human serum. These clones were then purified, excised in vitro, and converted into pBK-CMV plasmid forms, using the manufacturer's instructions. The inserted DNA was then evaluated using EcoRI-XbaI restriction mapping to determine different inserts. Eight different inserts were identified, ranging in size from about 500 to about 1.3 kilobase pairs. The clones were sequenced using an ABI PRISM automated sequencer.

Table 1 summarizes the results. One gene was represented by four overlapping clones, a second by three overlapping clones, and the remaining six by one clone only.

A homology search revealed that the clones referred to as NY-ESO-2, 3, 6, 7 were already known. See Elisei, et al., J. Endocrin. Invest. 16: 533–540 (1993); Spritz, et al., Nucl. Acids Res. 15: 10373–10391 (1987); Rabbits, et al., Nature Genetics 4: 175–180 (1993); Crozat, et al., Nature 363: 640–644 (1993); GenBank H18368 and D25606. Two of the clones (NY-ESO-3 and NY-ESO-6), have previously been shown to be expressed in various normal human tissues. No evidence of lineage restriction has been found. NY-ESO-6 (cDNA), appears to be the 3'-untranslated portion of the FUS/TLS gene. In experiments not reported here, sequencing and Southern Blot analysis of NY-ESO-6 showed no evidence of translocation or point mutations in the cancer. Four of the clones, i.e., NY-ESO-1, 4, 5 and 8 showed no strong homology to sequences in the databases examined, and were thus studied further.

TABLE 1

Genes isolated from esophageal cancer library by immunoscreening with autologous serum

| GENE | CLONE# | Size | DNA databank | Comments |
|---|---|---|---|---|
| NY-ESO-1 | E1-5b | 679 bp | No strong homology | expressed in testis and ovary |
|  | E1-114b | 614 bp |  |  |
|  | E1-153c | 670 bp |  |  |
|  | E1-50 | 679 bp |  |  |
| NY-ESO-2 | E1-71a | 605 bp | U1 small nuclear RNP 1 homolog | cloned by Ab screening (thyroiditis patient) |
|  | E1-140 | 874 bp |  |  |
|  | E1-31 | 750 bp |  |  |
| NY-ESO-3 | E1-141b | 517 bp | Colon 3' direct MboI cDNA; Adult brain cDNA | (dbj D25606, gb H18638) unpublished |
| NY-ESO-4 | E1A-10c | 400 bp | No strong homology | ubiquitous expression in normal tissues |
| NY-ESO-5 | E1A-54 | 670 bp | No strong homology | expressed in normal esophagus |
| NY-ESO-6 | E1B-9b | ~1.2 kb | Human fus mRNA | translocated in liposarcoma t (12;16) |
| NY-ESO-7 | E1B-20f | ~1.0 kb | human U1-70 k sn RNP | different from NY-ESO-2 (embl HSU17052, gbM22636) |
| NY-ESO-8 | E1B-20g | ~1.3 kb | No strong homology | ubiquitous expression in normal tissues |

EXAMPLE 3

Studies were carried out to evaluate mRNA expression of the NY-ESO 1, 4, 5 and 8 clones. To do this, specific oligonucleotide primers were designed for each sequence, such that cDNA segments of 300–400 base pairs could be amplified, and so that the primer melting temperature would be in the range of 65–70° C. Reverse transcription-PCR was then carried out using commercially available materials and standard protocols. A variety of normal and tumor cell types were tested. The clones NY-ESO-4 and NY-ESO-8 were ubiquitous, and were not studied further. NY-ESO-5 showed high level expression in the original tumor, and in normal esophageal tissue, suggesting that it was a differentiation marker.

NY-ESO-1 was found to be expressed in tumor mRNA and in testis, but not normal colon, kidney, liver or brain tissue. This pattern of expression is consistent with other tumor rejection antigen precursors.

EXAMPLE 4

The RT-PCR assay set forth supra was carried out for NY-ESO-1 over a much more complete set of normal and tumor tissues. Tables 2, 3 and 4 show these results. In brief, NY-ESO-1 was found to be highly expressed in normal testis and ovary cells. Small amounts of RT-PCR production were found in normal uterine myometrium, and not endometrium, but the positive showing was not consistent. Squamous epithelium of various cell types, including normal esophagus and skin, were also negative.

When tumors of unrelated cell lineage were tested, 2 of 11 melanomas cell lines showed strong expression, as did 16 of 67 melanoma specimens, 6 of 33 breast cancer specimens and 4 of 4 bladder cancer. There was sporadic expression in other tumor types.

TABLE 2 mRNA distribution of NY-ESO-1 in normal tissues

| Tissue | mRNA | Tissue | mRNA |
|---|---|---|---|
| Esophagus | – | Adrenal | – |
| Brain* | – | Pancreas | – |
| Fetal Brain | – | Seminal Vesicle | – |
| Heart | – | Placenta | – |
| Lung | – | Thymus | – |
| Liver | – | Lymph node | – |
| Spleen | – | Tonsil | – |
| Kidney | – | PBL | – |
| Stomach | – | PBL, activated# | – |
| Small intestine | – | Melanocytes | – |
| Colon | – | Thyroid | – |
| Rectum | – | Uterus | +/–** |
| Breast | – | Testis | + |
| Skin | – | Ovary | + |

*tissues from several parts tested with IL-2 and PHA
**weakly positive in some specimens, negative by Northern blot

TABLE 3 mRNA distribution of NY-ESO-1 in melanoma and breast cancer cell lines:

| Cell line | NY-ESO-1 mRNA |
|---|---|
| MZ2-MEL3.1 | – |
| MZ2-MEL2.2 | – |
| SK-MEL-13 | – |
| SK-MEL-19 | + |
| SK-MEL-23 | – |
| SK-MEL-29 | – |
| SK-MEL-30 | – |
| SK-MEL-31 | – |
| SK-MEL-33 | – |
| SK-MEL-37 | + |
| SK-MEL-179 | – |
| SK-BR-3 | – |
| SK-BR-5 | – |
| 734B | – |
| MDA-MB-231 | – |

TABLE 4

NY-ESO-1 mRNA expression in various human tumors by RT-PCR

| tumor type | mRNA (positive/total) | tumor type | mRNA (positive/total) |
|---|---|---|---|
| melanoma | 25/77 | ovarian cancer | 2/8 |
| breast cancer | 17/43 | thyroid cancer | 2/5 |
| prostate cancer | 4/16 | bladder cancer | 9/13 |
| colon cancer | 0/16 | Burkitt's lymphoma | ½ |
| glioma | 0/15 | basal cell carcinoma | 0/2 |
| gastric cancer | 0/12 | Jejomyosarcoma | 0/2 |
| lung cancer | 5/17 | other sarcomas | 0/2 |
| renal cancer | 0/10 | pancreatic cancer | 0/2 |
| lymphoma* | 0/10 | seminoma | 0/1 |
| hepatoma | 2/7 | spinal cord tumor | 0/1 |

*non-Hodgkin's, non-Burkitt's types.

A further set of experiments were carried out to ascertain if the presence of anti NY-ESO-1 antibody in cancer patient sera could be determined via an ELISA.

To elaborate, recombinant NY-ESO-1 in a solution of coating buffer (15 mM $Na_2CO_3$, 30 mM $NaHCO_3$, pH 9.6, 0.02% $NaN_3$), at a concentration of 1 ug/ml, was adsorbed to microwell plates (10 ul of solution per well), and then kept overnight at 4° C. The plates were washed with phosphate buffered saline, and blocked, overnight, at 4° C., with 10 ul/well of 2% bovine serum albumin/phosphate buffered saline. After washing, 10 ul/well of diluted serum in 2% bovine serum albumin was added to the wells. Following two hours of incubation at room temperature, plates were washed, and 10 ul/well of goat anti-human IgG-alkaline phosphatase conjugates were added, at a 1:1500 dilution. This solution was incubated for one hour at room temperature, followed by washing and addition of a solution of substrate for the alkaline phosphatase (10 ul/well). After 25 minutes at room temperature, the wells were read with a fluorescence plate reader. The results are presented in the following table:

| Cancer patients: | Eso 1+/total tested | % |
|---|---|---|
| melanoma | 12/127 | 9.4 |
| ovarian cancer | 4/32 | 12.5 |
| lung cancer | 1/24 | 4.0 |
| breast cancer | 2/26 | 7.7 |
| Blood donors | 0/70 | 0 |

In order to determine whether there was a relationship between expression of mRNA for NY-ESO-1 in tumors, and antibody response to the NY-ESO-1 protein, data from sixty-two melanoma patients were compared. All patients whose serum was reactive with NY-ESO-1 protein (i.e., contained antibodies to NY-ESO-1), also had NY-ESO-1 positive tumors, while no patients with NY-ESO-1 negative tumors showed antibodies to NY-ESO-1 in their serum. There was a percentage of NY-ESO-1 positive patients who lacked the antibody. Given that about 20–40% of melanomas expressed NY-ESO-1, and only patients with NY-ESO-1 positive tumors have antibody, the data suggest a high-percentage of patients with NY-ESO-1 positive tumors develops antibodies against the protein, thus suggesting a broad scale assay useful in diagnosis and responsiveness to treatment.

EXAMPLE 5

Northern blot analysis was then carried out to investigate the size of the NY-ESO-1 transcript, and to confirm tissue expression patterns. The methodology of Ausubel, et al., *Current Protocols In Molecular Biology* (John Wiley & Sons, 1995) was used. To be specific, 20 ug of total RNA per lane were dissolved in a formamide and formaldehyde containing buffer, heated to 65° C., and then separated on a 1.2% agarose gel, with 3% formaldehyde, followed by transfer to nitrocellulose paper. Hybridization was then carried out using a $^{32}P$ labelled probe, followed by high stringency washing. The final wash was at 0.1×SSC, 0.1% SDS, 60° C., for 15 minutes.

RNA from testis, and a melanoma cell line (SK-MEL-19) which had been positive for NY-ESO-1 in the prior assays, showed an RNA transcript of about 0.8–0.9 kb. An esophageal carcinoma specimen showed a smear in the 0.4–0.9 kb range, reflecting partial degradation. RNA from additional tissues or cell lines tested showed no transcript.

To get cDNA encoding the full transcript, the esophageal cDNA library was rescreened, using plaque hybridization, and the original cDNA clone as the hybridization probe. When $3 \times 10^5$ clones were screened, six positives were found. The three longest clones were sequenced. Analysis of open reading frames showed that all three contained the entire coding region, and 5'-untranslated regions of variable size. The longest clone, 755 base pairs in length, (excluding polyA), contains a 543 base pair coding region, together with 53 untranslated bases at the 5' end and 151 untranslated base pairs at the 3'-end. See SEQ ID NO: 1 (also, FIG. 3).

The long ORF indicated that the deduced sequence of NY-ESO-1 protein is 180 amino acids. The single immunopositive clone contained a sequence encoding 173 of these. Deduced molecular mass is 17,995 daltons.

Analysis shows that there is an abundance of glycine residues in the N-terminal portion (30 of the first 80, 4 in the remaining 100). Hydrophilicity analysis indicated that there were hydrophilic antigenic sequences in the N-terminal half of the molecule, with alternating hydrophobic and hydrophilic sequences, ending with a long, C-terminal hydrophobic tail (amino acids 152–172), followed by a short hydrophilic tail. This pattern suggests a transmembrane domain. There are several potential N-myristorylation sites, 3 phosphorylation sites, and no evidence of N-glycosylation sites.

EXAMPLE 6

A melanoma cell line "NW-MEL-38" was established, in 1995, from a patient who suffered from malignant melanoma. Serum samples, peripheral blood lymphocytes, and tumor samples, were taken from the subject and frozen, until the work described herein was carried out. In anticipation of evaluating antitumor T cell response in this patient, the patient was HLA typed as HLA-A1 and HLA-A2.

To determine whether melanoma from this patient expressed NY-ESO-1, total RNA was isolated from both tumor samples and cell line NW-MEL-38, using standard techniques. Then, two micrograms of the total RNA, from each samples were subjected to cDNA synthesis, again using standard techniques.

The cDNA was then used in RT-PCR experiments, using the following primers:

5'-CACACAGGAT CCATGGATGC TGCAGATGCG G'-3', (SEQ ID NO: 2)

and

CACACAAAGC TTGGCTTAGC GCCTCTGCCC TG-3' (SEQ ID NO: 3)

These primers should amplify a segment of SEQ ID NO: 1 which spans nucleotides 271 to 599.

Amplification was carried out over 35 cycles, using an annealing temperature of 60° C. The PCR products were visualized via ethidium bromide staining, on a 1.5% agarose gel.

The results indicated that both the tumor and the cell line expressed SEQ ID NO: 1. The cell line and tumor samples were used in subsequent experiments.

EXAMPLE 7

The isolated cDNA molecule, discussed supra, was then used to make recombinant protein. Specifically, the cDNA was PCR amplified, using standard techniques, and was then cloned into a commercially available plasmid vector, i.e., pQE9, which contains His tags. In work not elaborated upon herein, a second vector, pQE9K was also used. This differs from PQE9 in that kanamycin resistance is imparted by pQE9K, rather than. ampicillin resistance.

The plasmid vector was transformed into *E. coli* strain XL1-Blue, and positive transformants were identified via restriction mapping and DNA sequencing. Production of recombinant protein was induced using isopropyl β-D-thiogalactoside, and the protein was purified on an $Ni^{2+}$ ion chromatography column, following well known procedures. The protein when analyzed via 15% SDS-PAGE and silver staining, was identified as a protein with a molecular weight of about 22 kilodaltons. This is consistent with the anticipated size of the protein from its sequence. Two other forms of the recombinant protein were also identified. These consisted of amino acids 10–180, and 10–121 of the amino acid sequence reported in SEQ ID NO: 1. They have molecular weights of about 14 kD and 20 kD, respectively, on SDS-PAGE, as carried out supra.

An additional set of experiments were carried out to express NY-ESO-1 in baculovirus. To elaborate, the NY-ESO-1 cDNA insert was released from the pQE9 vector, by cleavage with BamHI and HindIII. This insert was then subcloned into a commercially available baculovirus vector which had been cleaved with the same enzymes. Positive clones were determined, using standard methods, and transfected into recipient Sf9 cells. Recombinant viruses were then used to infect insect cells, using a standard medium (IPL-41), supplemented with 10% fetal calf serum. The multiplicity of infection for the work was 20. Expression of recombinant protein was determined as described supra. The recombinant protein produced in this vector carries an His-tag, so it was purified on $Ni^{2+}$ affinity columns, also as described, supra. The protein consists of amino acids 10–180, and has a molecular weight of 20 kD via SDS-PAGE.

Additional eukaryotic transfectants were then produced. To do this, the NY-ESO-1 coding sequence was isolated from the pQE9 vector described supra, and then cloned into BamHI-HindIII sites of eukaryotic expression vector pcDNA 3.1. Next, COS-7 cells were transfected with this vector, by contacting cell samples with 150 ng of the plasmid discussed supra, and 150 ng of plasmid pcDNA 1 Amp, which contained either cDNA for HLA-A2.1 or cDNA for HLA-A1, The well known DEAE-dextran chloroquine method was used. The cells were then incubated at 37° C., for 48 hours, after which they were tested in a CTL stimulation assay. Specifically, the assay followed Traversari et al, Immunogenetics 35: 145–148 (1992), incorporated by reference. In brief, 2500 CTLs, (NW38-IVS-1, see example 9, infra), in 100 ul RPMI supplemented with 100% human serum, and 25 U/ml of recombinant IL-2 were added to microwells containing COS-7 transfectants (20,000 cells/well). After 24 hours, 50 ul of supernatant were collected from each well, and TNF-α levels were determined in a standard assay, i.e., one where cytotoxicity against WEHI 164 clone 13 cells were tested, using MTT. Positive cells were used in the Western Blot analysis, described in the example which follows.

The CTLs used were CTL NW38-IVS-1, prepared in accordance with Knuth et al., Proc. Natl. Acad. Sci. USA 81: 3511–3515 (1984), incorporated by reference. Specifically, mixed lymphocyte T cell cultures were set up, by combining $10^5$ autologous NW38 MEL-1 tumor cells, and $10^6$ peripheral blood lymphocytes, taken from the subject. The cytokine IL-2 was added, and the mixed culture was incubated for one week at 37° C. Tumor cells were removed, and a new aliquot of $5\times10^4$ tumor cells were added together with IL-2. This process was repeated weekly, until a strong response was seen when tested against $^{51}Cr$ labelled NW-MEL-38 cells. The responder T cells were collected and frozen until used in further experiments.

EXAMPLE 8

Western Blot analysis was then carried out, using the serum samples described supra, as well as cell lysates taken from the cell line NW-MEL-38, described supra, and the COS-7 transfectants, described supra, and the purified recombinant protein, also described supra. Serum samples were taken from various points of the patient's therapy. There was no difference in the results.

In these assays, 1 ug of recombinant NY-ESO-1 protein, or 5 ul of cell lysates of either type were diluted in SDS and boiled for five minutes, and then electrophoresed on a 15% SDS gel. After overnight blotting on nitrocellulose (0.45 um), and blocking with 3% BSA, the blots were incubated with serum, diluted at 1:1000, 1:10,000, and 1:100,000, or with a monoclonal antibody against NY-ESO-1, diluted to 1:50, as a positive control. The monoclonal antibody was prepared via Chen, et al., Proc. Natl. Acad. Sci. USA 5915–5919 (1996), incorporated by reference and elaborated as follows. BALB/C mice were immunized via five subcutaneous injections of recombinant NY-ESO-1 protein, at 2–3 week intervals. The immunizing formulation included 50 ug of recombinant protein in adjuvant. The first injection used Complete Freund's Adjuvant, and Incomplete Freund's Adjuvant was used thereafter. Spleen cells were taken from the immunized mice, and fused with mouse myeloma cell line SP2/0, to generate hybridomas. Representative hybridoma E978 was used for generation of mAbs.

Once hybridomas were generated, they were cloned, and their supernatants were screened against recombinant protein, using a standard solid phase ELISA on microtiter plates. The assay was in accordance with Dippold et al., Proc. Natl. Acad. Sci. USA 77: 6114–6118 (1980), incorporated by reference. A series of negative controls were also run, using recombinant NY-ESO-1. Serum antibodies which bound to recombinant protein, produced by E. coli as described, supra were visualized using goat anti-human IgG, labelled with alkaline phosphatase at 1:10,000 dilution, and were then visualized with NBT-phosphate. Untransfected COS-7 cells were also used as a control. Serum from a healthy individual was also used as a control.

Strong reactivity against the recombinant protein was found at serum dilutions down to 1:100,000, and there was also reactivity against lysate of NW-MEL-38. There was no reactivity found against the untransfected COS-7 cells, nor did the serum from a healthy individual show reactivity.

EXAMPLE 9

Four different forms of NY-ESO-1 are described supra, i.e., the form produced by SEQ ID NO: 1 in E. coli, as well as one consisting of amino acids 10–180, one consisting of amino acids 10–121, and a form, expressed in the baculovirus vector system discussed supra which consisted of amino acids 10–180. Each form was used in ELISAs, following the above described protocols. All forms of the protein were found to be equally reactive with antibodies taken from various patients, as well as the murine monoclonal antibodies discussed, supra.

EXAMPLE 10

In the testing of the COS-7 transfectants, supra, and the assays discussed in this example, a cytolytic T cell line "NW38-IVS-1" was used. This "CTL" was generated, via in vitro stimulation of the peripheral blood lymphocytes mentioned supra, using the tumor cell line NW-MEL-38. This was done using standard techniques.

Figure 5:
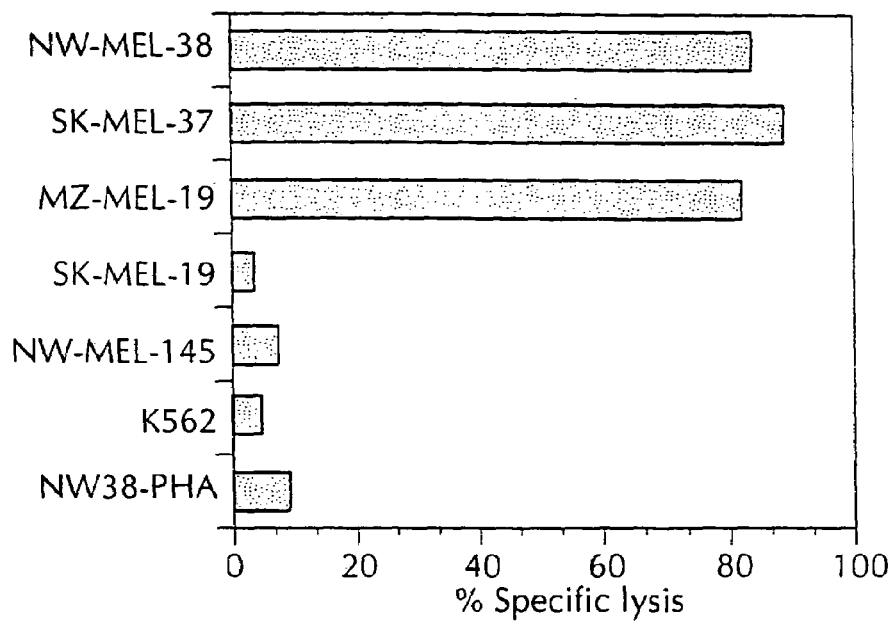
FIG. 5 shows the results of CTL lysis studies using various cells which are HLA-A2 positive, NY-ESO-1 positive, positive for both, or positive for neither.

The CTL was used in a cytotoxicity assay with NW-MEL-38 (which was HLA-A1, A2 positive, and NY-ESO-1 positive), along with two allogeneic cell lines which were NY-ESO-1 and HLA-A2 positive (SK-MEL-37 and MZ-MEL-19), a cell line which is MHC Class I negative (SK-MEL-19), a cell line which is HLA-A2 positive, but NY-ESO-1 negative (NW-MEL-145), along with control cell lines K562 and autologous phytohemagglutinin stimulated blasts. Various effector/target ratios were used, and lysis of $^{51}Cr$ labelled target cells was the parameter measured. FIG. 5 shows this.

Figure 6:
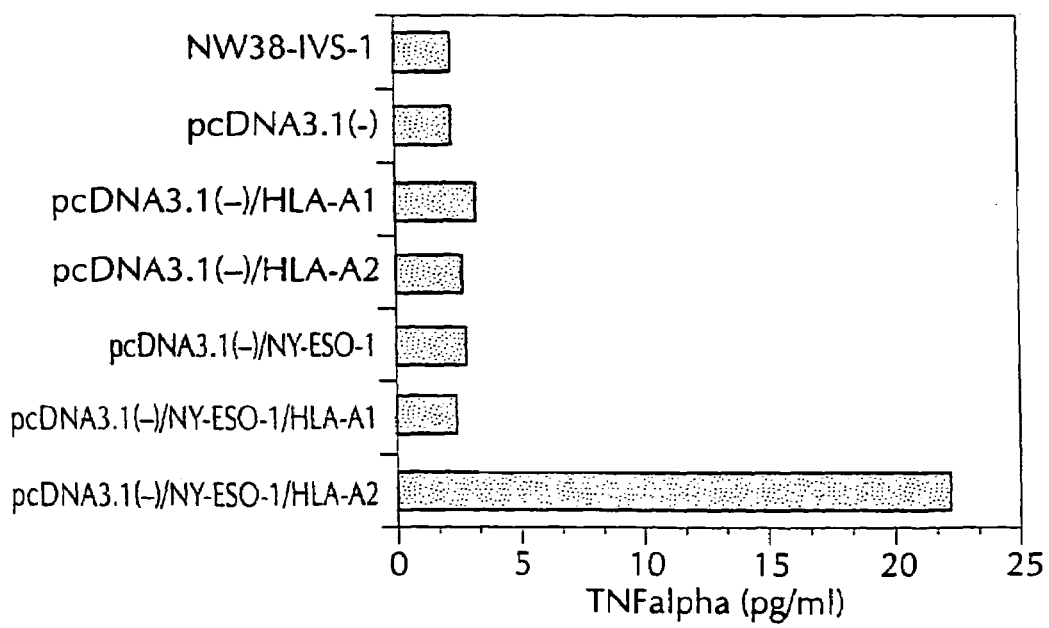
FIG. 6 presents data establishing that HLA-A2 is the presenting molecule for presentation of SEQ ID NO: 1 derived peptides.

The results indicated that the CTL NW38-IVS-1 lysed both the autologous cell line NW MEL-38, and the allogeneic cell lines which were HLA-A2 and ESO-1 positive. Hence, the CTL was reactive with allogeneic materials. See FIG. 6.

EXAMPLE 11

As patient NW38 was HLA-A1 and HLA-A2 positive, experiments were carried out to determine which MHC molecule was the presenting molecule.

The same experiment, described supra with COS-7 cells was carried out, except that, in these experiments, care was taken to secure separate groups of cotransformants which had been transformed with either HLA-A1 cDNA, or HLA-A2 cDNA, but not both. These results show that the CTL NW38-IVS-1 lysed COS-7 transfectants containing both NY-ESO-1 and HLA-A2 exclusively. See FIG. 6. The work also confirmed the specificity of the CTL, since the NY-ESO-1 negative, HLA-A2 positive cells described in Example 9 were positive for other molecules known to be processed to peptides presented by HLA-A2 molecules.

EXAMPLE 12

Once the presenting MHC molecule was identified as HLA-A2, a screening of the amino acid sequence for NY-ESO-1 was carried out, to identify all peptides which satisfy this motif, using the model set forth by D'Amaro et al., Human Immunol. 43: 13–18 (1995), and Drijfhout, et al., Human Immunol. 43: 1–12 (1995) incorporated by reference. Peptides corresponding to all of the amino acid sequences deduced thereby were synthesized, using standard techniques, and were then used in cytotoxicity assays, following Knuth et al., Proc. Natl. Acad. Sci. USA 81: 3511–3515 (1984), incorporated by reference. Specifically, cell line CEMX721.174.T2 ("T2" hereafter), was used, because it does not process antigens to MHC complexed peptides, thereby making it ideal for experiments of the type described herein. Samples of T2 cells were labelled with 100 uCi of Na($^{51}$Cr)O$_4$, using standard methods, and were then washed three times, followed by incubation with 10 ug/ml peptide and 2.5 ug/ml of β2-microglobulin. Incubation was for one hour, at room temperature. Then responder cells (100 ul of a suspension of CTL NW38-IVS-1) were added, at an effector/target ratio of 90:1, and incubated for four hours in a water saturated atmosphere, with 5% CO$_2$, at 37° C. Then, plates were centrifuged at 200×g for five minutes, 100 ul of supernatant was removed, and radioactivity was measured. The percentage of $^{51}$Cr release was determined in accordance with known strategies. it was found that the peptides SLLMWITQCFL (SEQ ID NO: 4), SLLMWITQC (SEQ ID NO: 5), and QLSLLMWIT (SEQ ID NO: 6), were the three best stimulators of CTLs. Comparable results were found when NW-MEL-38 and cell lines SK-MEL-37 and MZ-MEL-19 were used as targets, as is shown, supra.

EXAMPLE 13

The amino acid sequence of the protein encoded by SEQ ID NO: 1 was analyzed for peptide sequences which correspond to HLA binding motifs. This was done using the algorithm taught by Parker et al., J. Immunol. 142: 163 (1994), incorporated by reference. In the Table which follows, the amino acid sequence, the HLA molecule to which it presumably binds, and the positions in SEQ ID NO: 1 are given. The resulting complexes should provoke a cytolytic T cell response. This could be determined by one skilled in the art following methods taught by, e.g., van der Bruggen, et al., J. Eur. J. Immunol. 24: 3038–3043 (1994), incorporated by reference.

| Sequence | MHC/HLA Molecule | Positions |
| --- | --- | --- |
| GPESRLLEF | HLA-A1 | 82–90 |
| LLMWITQCF | HLA-A3 | 158–166 |
| LMWITQCFL | HLA-A3 | 159–167 |
| EPTVSGNIL | HLA-A24 | 125–133 |
| LQLSISACL | HLA-A24 | 145–153 |
| GARGPESRL | HLA-B7 | 79–87 |
| APRGPHGGA | HLA-B7 | 60–68 |
| ESRLLEFYL | HLA-B7 | 84–92 |
| APPLPVPGV | HLA-B7 | 113–121 |
| FATPMEAEL | HLA-B7 | 96–104 |
| AADHRQLQL | HLA-B7 | 139–147 |
| GARGPESRL | HLA-B8 | 79–87 |
| ESRLLEFYL | HLA-B8 | 84–92 |
| VPGVLLKEF | HLA-B35 | 118–126 |
| ESRLLEFYL | HLA-B35 | 84–92 |
| GARGPESRL | HLA-B35 | 79–87 |
| LEFYLAMPF | HLA-B44 | 88–96 |
| PESRLLEFY | HLA-B44 | 83–91 |
| AELARRSLA | HLA-B44 | 102–110 |
| MEAELARRS | HLA-B44 | 100–108 |
| QQLSLLMWI | HLA-B52 | 154–162 |
| AQDAPPLPV | HLA-B52 | 110–118 |
| LQLSISSCL | HLA-B52 | 145–153 |
| ITQCFLPVF | HLA-B52 | 162–170 |
| LLEFYLAMPF | HLA-A1 | 87–96 |
| GPESRLLEFY | HLA-A1 | 82–91 |
| PLPVPGVLLK | HLA-A3 | 115–124 |
| RSLAQDAPPL | HLA-A24 | 107–116 |
| APPLPVPGVL | HLA-B7 | 113–122 |
| GARGPESRLL | HLA-B7 | 79–88 |
| GPHGGAASLG | HLA-B7 | 63–72 |
| APRGPHGAA | HLA-B7 | 60–69 |
| GPRGAGAARA | HLA-B7 | 44–53 |
| TAADHRQLQL | HLA-B8 | 138–147 |
| APPLPVPGVL | HLA-B52 | 113–122 |
| QQLSLLMWIT | HLA-B52 | 154–163 |
| LQQLSLLMWI | HLA-B52 | 153–162 |
| KEFTVSFNIL | HLA-B52 | 124–133 |

EXAMPLE 14

Further experiments were carried out to identify additional relevant peptides. In these experiments, a stable tumor cell line, i.e., MZ-MEL-19 was used. This cell line had been established from a patient referred to as MZ19, using methods described by Jäger, et al., J. Exp. Med 187:265–269

(1998), incorporated by reference. A cytolytic T cell line, i.e., MZ2-MEL 19-IVS-1 was also established, using MZ-MEL-19 and the methods set forth in example 7, supra, as well as Jäger et al., supra. This CTL lysed the autologous tumor cell line, in an HLA-A2 restricted fashion. This was determined using standard methods. The model set forth by D'Amaro, et al., supra, was used to identify all sequences in ESO-1 which satisfy HLA-A2 binding motifs. Twenty six peptides were identified in this way. All were synthesized, purified, and tested for integrity, using standard methods. The peptides were then synthesized, and tested in the experiments which follow. MZ19-IVS-1 was used, together with the T2 cells described in Example 12. The peptides of SEQ ID NO: ID NOS.: 4 and 5 bound to HLA-A2 molecules, and were recognized by CTL MZ19-IVS-1, which lysed the cells. This CTL also recognized complexes of HLA-A2 and the decapeptide:

LLMWITQCFL (SEQ ID NO.: 7), which is found at positions 156–167 of SEQ ID NO.: ID NO.1.

EXAMPLE 15

Further studies were carried out to determine if CD4⁺ helper T cells recognized complexes of MHC Class II molecules and peptides.

Tumor cell line MZ-MEL-19 has been types as being HLA-DR53 positive. Hence, NY-ESO-1 was screened using Futaki, et al., *Immunogenetics*, 42:299–301 (1995), incorporated by reference, which teaches binding motifs for HLA-DR53. A total of twenty-eight peptides which, in theory, would bind to HLA-DR53 were found.

Peripheral blood lymphocytes ("PBLs"), were isolated from two patients with metastatic melanoma, who had been typed as HLA-DR53 positive.

The typing was performed using standard, commercially available reagents. One patient was typed as being positive for HLA-DRB1 (alleles 1501–05, 1601–1603, 1605 and 0701), HLA DRB4* (alleles (0101–0103), and DRB5* (alleles 0101), while the second patient was typed as positive for HLA-DRB1* (alleles 1401, 1407, 1408, and 0901), HLA-DRB3* (alleles 0201–0203), and DRB4* (alleles 0101–0103). All alleles of HLA-DRB4* are referred to as HLA-DR53, in accordance with Bodmer, et al., Human Immunol 34:4–18 (1992), incorporated by reference.

The PBLs were treated with magnetic beads coated with appropriate antibodies to deplete CD4+ and CD8+ T lymphocytes. The remaining cells were seeded in 24 well plates, at 4×10⁶ cells/well, and were allowed to adhere to the plastic of the wells for 24 hours. Any non-adhering cells were removed, and the remaining cells were used as antigen presenting cells. These cells were stimulated with GM-CSF (1000 U/ml), and IL-4 (1000 U/ml) for 5 days, in 96-well, flat bottom nitrocellulose plates, which had been coated, overnight, at 4° C., with 5 ug/ml of anti-gamma interferon antibodies. Cells were seeded at 3.5×10⁵ cells/well.

The cells were then pulsed with 4 ug/well of test peptide, or 2 ug/well of the complete NY-ESO-1 protein, as a control.

Then CD4+ T cells were added (1×10⁵) cells/well, in RPMI 1640 medium augmented with 10% human serum, L-asparagine (50 mg/l), L-arginine (242 mg/l), and L-glutamine (300 mg/l), together with 2.5 ng/ml of IL-2, to a final volume of 100 ul).

This mixture was incubated for 48 hours at 37° C. in a water saturated atmosphere. Then, plates were washed, 6 times, with a solution of 0.05% Tween 20/PBS, and then biotinylated anti-interferon gamma antibody, was added at 0.5 ug/ml. The antibody was incubated for 2 hours at 37° C., after which plates were developed with standard reagents, for 1 hour. Substrate 3-ethyl-9-amino carbazole was added, and incubated for 5 minutes, with positives being represented by red spots. The number of red spots/well was indicative of the frequency of CD4+ T lymphocytes which recognized complexes of peptide and HLA-DR53, or HLA-DR53 and a peptide processed from recombinant NY-ESO-1. As controls, assays were run using reagents alone (i.e., CD4+ cells alone, and the stain alone.

The following peptides were found to sensitize the CD4+ T lymphocytes to release gamma interferon.

```
AADHRQLQLSISSCLQQL    (SEQ ID NOS. 8-10)

VLLKEFTVSGNILTIRLT

PLPVPGVLLKEFTVSGNI
```

These three peptides satisfy the motif for binding to HLA-DR53 set forth by Futaki, et al., supra, which is an anchor residue of Tyr, Phe, Trp, or Leu, followed by Ala or Ser three residues downstream.

Additional peptides were found which bind to HLA-DR53.

These peptides are:

```
GAASGLNGCCRCGARGPE    (SEQ ID NOS. 11-13)

SRLLEFYLAMPFATPMEA

TVSGNILTIRLTAADHRQ.
```

The foregoing examples describe the isolation of a nucleic acid molecule which encodes an esophageal cancer associated antigen. "Associated" is used herein because while it is clear that the relevant molecule was expressed by esophageal cancer, other cancers, such as melanoma, breast, prostate and lung also express the antigen.

The invention relates to those nucleic acid molecules which encode antigens as described, and which hybridize to reference sequence SEQ ID NO: 1 under stringent conditions. "Stringent conditions" as used herein refers to conditions such as those specified in U.S. Pat. No. 5,342,774, i.e., 18 hours of hybridization at 65° C., followed by four one hour washes at 2×SSC, 0.1% SDS, and a final wash at 0.2×SSC, more preferably 0.1×SSC, 0.1% SDS for 30 minutes, as well as alternate conditions which afford the same level of stringency, and more stringent conditions.

Also a part of the invention are expression vectors which incorporate the nucleic acid molecules of the invention, in operable linkage (i.e., "operably linked") to a promoter. Construction of such vectors is well within the skill of the art, as is the transformation or transfection of cells, to produce eukaryotic cell lines, or prokaryotic cell strains which encode the molecule of interest. Exemplary of the host cells which can be employed in this fashion are COS cells, CHO cells, yeast cells, insect cells (e.g., *Spodoptera frugiperda*), NIH 3T3 cells, and so forth. Prokaryotic cells, such as *E. coli* and other bacteria may also be used.

Also a part of the invention is the antigen described herein, both in original peptide form and in post translational modified form, as well as proteins consisting of at least amino acids 10–121, and no more than 10–180, of the protein encoded by SEQ ID NO: 1. The molecule is large enough to be antigenic without any posttranslational modification, and hence it is useful as an immunogen, when combined with an adjuvant (or without it), in both precursor and post-translationally modified forms. These proteins can be used to determine whether or not antibodies are present in a sample, such as serum or blood, as shown supra. The antibodies produced using this antigen, both poly and monoclonal, are also a part of the invention as well as hybridomas which make the monoclonal antibody. These can be used therapeutically or diagnostically as the whole molecule or in portions, as discussed infra. Also a part of the invention are reactive fragments, such as Fab, F(ab)$_2$' and other fragments, as well as chimeras, humanized antibodies, recombinantly produced antibodies, and so forth. Especially preferred are chimeras where the entire antibody but the complementarity determining regions "CDRS" is human, but the CDRs are murine.

As is clear from the disclosure, one may use the proteins and nucleic acid molecules of the invention diagnostically. The SEREX methodology discussed herein is premised on an immune response to a pathology associated antigen. Hence, one may assay for the relevant pathology via, e.g., testing a body fluid sample of a subject, such as serum, for reactivity with the antigen per se. Reactivity would be deemed indicative of possible presence of the pathology so, too, could one assay for the expression of the antigen via any of the standard nucleic acid hybridization assays which are well known to the art, and need not be elaborated upon herein. One could assay for antibodies against the subject molecule, using standard immuno assays as well.

Analysis of SEQ ID NO: 1 will show that there are 5' and 3' non coding regions presented therein. The invention relates to those isolated nucleic acid molecules which contain at least the coding segment, i.e., nucleotides 54–593, and which may contain any or all of nucleotides 1–53 and/or 594–747 of SEQ ID NO: 1.

Further analysis, as discussed supra, reveals that the molecule is processed to peptides which provoke lysis by cytolytic T cells. Example 7 showed how this type of motif analysis can be carried out for HLA-A2 molecules. There has been a great deal of work in motifs for various MHC or HLA molecules, which is applicable here. Hence, a further aspect of the invention is a therapeutic method, wherein one or more peptides which bind to an HLA molecule on the surface of a patient's tumor cells are administered to the patient, in an amount sufficient for the peptides to bind to the MHC/HLA molecules, and provoke lysis by T cells. The exemplification given supra for HLA-A2 molecules is by no means the only type of this administration that can be used. Any combination of peptides may be used, such as those for other HLA molecules, described supra. These peptides, which may be used alone or in combination, as well as the entire protein or immunoreactive portions thereof, may be administered to a subject in need thereof, using any of the standard types of administration, such as intravenous, intradermal, subcutaneous, oral, rectal, and transdermal administration. Standard pharmaceutical carriers, adjuvants, such as saponins, GM-CSF, and interleukins and so forth may also be used. Further, these peptides and proteins may be formulated into vaccines with the listed material, as may dendritic cells, or other cells which present relevant MHC/peptide complexes. These peptides may also be used to form multimeric complexes of HLA/peptides, such as those described by Dunbar, et al., Curr. Biol. 8: 413–416 (1998), incorporated by reference, wherein four peptide/MHC/biotin complexes are attached to a streptavidin or avidin molecule. Such complexes can be used to identify and/or to stimulate T cell precursors.

Similarly, the invention contemplates therapies wherein the nucleic. acid molecule which encodes NY-ESO-1 is incorporated into a vector, such as an adenovirus based vector, to render it transfectable into eukaryotic cells, such as human cells. Similarly, nucleic acid molecules which encode one or more of the peptides may be incorporated into these vectors, which are then the major constituent of nucleic acid bases therapies.

Any of these assays can also be used in progression/regression studies. One can monitor the course of abnormality involving expression of NY-ESO-1, simply by monitoring levels of the protein, its expression, and so forth using any or all of the methods set forth supra.

It should be clear that these methodologies may also be used to track the efficacy of a therapeutic regime. Essentially, one can take a baseline value for the NY-ESO-1 protein, using any of the assays discussed supra, administer a given therapeutic agent, and then monitor levels of the protein thereafter, observing changes in ESO-1 levels as indicia of the efficacy of the regime.

As was indicated supra, the invention involves, inter alia, the recognition of an "integrated" immune response to the NY-ESO molecule. One ramification of this is the ability to monitor the course of cancer therapy. In this method, which is a part of the invention, a subject in need of the therapy receives a vaccination of a type described herein. Such a vaccination results, e.g., in a T cell response against cells presenting HLA/peptide complexes on their cells. The response also includes an antibody response, possibly a result of the release of antibody provoking proteins via the lysis of cells by the T cells. Hence, one can monitor the effect of a vaccine, by monitoring an immune response. As is indicated, supra, an increase in antibody titer or T cell count may be taken as an indicia of progress with a vaccine, and vice versa. Hence, a further aspect of the invention is a method for monitoring efficacy of a vaccine, following administration thereof, by determining levels of antibodies in the subject which are specific for the vaccine itself, or a large molecules of which the vaccine is a part.

The effects of a vaccine can also be measured by monitoring the T cell-response of the subject receiving the vaccine. A number of assays can be used to measure the precursor frequency of these in vitro stimulated T cells. These include, but are not limited to, chromium release assays, TNF release assays, IFNγ release assays, an ELISPOT assay, and so forth. Changes in precursor T cell frequencies can be measured and correlated to the efficacy of the vaccine. Additional methods which can be employed include the use of multimeric complexes of MHC/peptides. An example of such complexes is the tetrameric HLA/peptide-biotin-streptavidin system of Dunbar, et al. Curr. Biol. 8: 413–416 (1998), incorporated by reference.

The identification of NY-ESO-1 proteins as being implicated in pathological conditions such as cancer also suggests a number of therapeutic approaches in addition to those discussed supra. The experiments set forth supra establish that antibodies are produced in response to expression of the protein. Hence, a further embodiment of the invention is the treatment of conditions which are characterized by aberrant or abnormal levels of NY-ESO-1 proteins, via administration of antibodies, such as humanized antibodies, antibody fragments, and so forth. These may be tagged or labelled with appropriate cystostatic. or cytotoxic reagents.

T cells may also be administered. It is to be noted that the T cells may be elicited in vitro using immune responsive cells such as dendritic cells, lymphocytes, or any other immune responsive cells, and then reperfused into the subject being treated.

Note that the generation of T cells and/or antibodies can also be accomplished by administering cells, preferably treated to be rendered non-proliferative, which present relevant T cell or B cell epitopes for response, such as the epitopes discussed supra.

The therapeutic approaches may also include antisense therapies, wherein an antisense molecule, preferably from 10 to 100 nucleotides in length, is administered to the subject either "neat" or in a carrier, such as a liposome, to facilitate incorporation into a cell, followed by inhibition of expression of the protein. Such antisense sequences may also be incorporated into appropriate vaccines, such as in viral vectors (e.g., Vaccinia), bacterial constructs, such as variants of the known BCG vaccine, and so forth.

Also a part of the inventions are peptides, which can be nonamers, decamers, or undecamers defined as having a core sequence:

LLMWIT (SEQ ID NO: 14)

which have at least one additional residue terminal to the first L residue, preferably serine and may have as many as three, wherein Serine is linked to L to form -SL-, and 0–4 additional amino acids at the C-terminus which, as shown supra, bind to HLA-A2 molecules, thereby provoking a CTL response. These peptides may be used therapeutically, via administration to a patient who is HLA-A2 positive, and expresses NY-ESO-1 in connection with a pathology, as well as diagnostically, i.e., to determine if HLA-A2 positive cells are present, or if relevant CTLs are present, and so forth.

The HLA-A2 molecule is an MHC Class I molecule, and T cells which respond to complexes of peptides and class I molecules are generally CD8$^+$ cells. Another subset of T cells, CD4$^+$ cells, responds to complexes of MHC-Class II molecules and peptides, and MHC-Class II restricted CD4$^+$ T cell responses against recombinant NY-ESO-1, presented by autologous cultured dendritic cells have been detected in melanoma patients. Specifically, in results not described herein, CD4$^+$ cells were separated from other cells from PBLs or serum samples, using well known techniques. Then, they were admixed with dendritic cells which had been pulsed with NY-ESO-1 protein. Proliferation of CD4$^+$ cells was observed, bringing another facet to the integrated immune response discussed herein. Hence, a further aspect of this invention are these CD4$^+$ T cells, peptides which bind to the MHC-Class II molecules, and their use in therapy.

Exemplary of the peptides defined by the core sequence of SEQ ID NO: ID NO.: 14 is the peptide defined by SEQ ID NO: ID NO.: 7. This peptide, as indicated, binds to HLA-A2 molecules. Hence it is a "marker" for HLA-A2, as well as a component of peptide/MHC complexes which stimulate proliferation of CTLs, as is described supra.

As the examples indicate, ESO-1 is also processed to peptides which complex to MHC Class II molecules, HLA-DR53 in particular. These molecules satisfy the motif described by Futaki, et al., supra, i.e., Tyr, Phe, Trp, or Leu, followed 3 amino acids later by Ala or Ser. Such peptides must be at least 18 amino acids long, and are preferably no more than 25 amino acids long. Preferably, they consist of 18 amino acids, such as SEQ ID NOS.: 8, 9, 10, 11, 12 and 13. These peptides serve to identify HLA-DR53 positive cells. Further, in the case of peptides such as SEQ ID NOS.: 8, 9 and 10, these can be used to provoke proliferation of helper T cells, as the examples show. All of the applications given supra for the MHC Class I restricted peptides are applicable to these Class II restricted peptides. Further, since the nature of the immune response is different with MHC-Class I/peptide complexes as compared to MHC-Class II/peptide complexes, one may combine both types of peptide, such as in immune compositions, thereby generating a combined immune response. Hence, all applications described can be used with just the Class I restricted peptides, with just the Class II restricted peptides, or with combinations of these.

Other features and applications of the invention will be clear to the skilled artisan, and need not be set forth herein.

The terms and expression which have been employed are used as terms of description and not of limitation, and there is no intention in the use of such terms and expression of excluding any equivalents of the features shown and described or portions thereof, it being recognized that various modifications are possible within the scope of the invention.

We claim:

1. An isolated nucleic acid molecule which encodes a polypeptide, the amino acid sequence of which is set forth at SEQ ID NO: 4, 5, 6, 7, 8, 9, 10, 11, or 12.

2. An expression vector comprising the isolated nucleic acid molecule of claim 1, operably linked to a promoter.

3. The isolated nucleic acid molecule of claim 1, wherein said isolated nucleic acid molecule encodes the polypeptide set forth at SEQ ID NO: 7.

4. An expression vector comprising the isolated nucleic acid molecule of claim 3, operably linked to a promoter.

5. A recombinant cell comprising the isolated nucleic acid molecule of claim 1.

6. A recombinant cell comprising the expression vector of claim 2.

7. A non-proliferative recombinant cell which expresses a complex of an MHC molecule and a polypeptide encoded by the isolated nucleic acid molecule of claim 1.

8. A composition comprising the non-proliferative recombinant cell of claim 7 and an adjuvant.

* * * * *

SEQUENCE LISTING (1) GENERAL INFORMATION:

(iii) NUMBER OF SEQUENCES: 15

(2) INFORMATION FOR SEQ ID NO: 1:

(i) SEQUENCE CHARACTERISTICS:
        (A) LENGTH: 752 base pairs
        (B) TYPE: nucleic acid
        (C) STRANDEDNESS: double
        (D) TOPOLOGY: linear (xi) SEQUENCE DESCRIPTION: SEQ ID NO: 1:

```
ATCCTCGTGG GCCCTGACCT TCTCTCTGAG AGCCGGGCAG AGGCTCCGGA GCC           53

ATG CAG GCC GAA GGC CGG GGC ACA GGG GGT TCG ACG GGC GAT GCT          98
Met Gln Ala Glu Gly Arg Gly Thr Gly Gly Ser Thr Gly Asp Ala
              5                  10                  15

GAT GGC CCA GGA GGC CCT GGC ATT CCT GAT GGC CCA GGG GGC AAT         143
```

-continued

```
                Asp Gly Pro Gly Gly Pro Gly Ile Pro Asp Gly Pro Gly Gly Asn
                            20                  25                  30

GCT GGC GGC CCA GGA GAG GCG GGT GCC ACG GGC GGC AGA GGT CCC             188
Ala Gly Gly Pro Gly Glu Ala Gly Ala Thr Gly Gly Arg Aly Pro
                35                  40                  45

CGG GGC GCA GGG GCA GCA AGG GCC TCG GGG CCG GGA GGA GGC GCC             233
Arg Gly Ala Gly Ala Ala Arg Ala Ser Gly Pro Gly Gly Gly Ala
                50                  55                  60

CCG CGG GGT CCG CAT GGC GGC GCG GCT TCA GGG CTG AAT GGA TGC             278
Pro Arg Gly Pro His Gly Gly Ala Ala Ser Gly Leu Asn Gly Cys
                65                  70                  75

TGC AGA TGC GGG GCC AGG GGG CCG GAG AGC CGC CTG CTT GAG TTC             323
Cys Arg Cys Gly Ala Arg Gly Pro Glu Ser Arg Leu Leu Glu Phe
                80                  80                  90

TAC CTC GCC ATG CCT TTC GCG ACA CCC ATG GAA GCA GAG CTG GCC             368
Tyr Leu Ala Met Pro Phe Ala Thr Pro Met Glu Ala Glu Leu Ala
                95                  100                 105

CGC AGG AGC CTG GCC CAG GAT GCC CCA CCG CTT CCC GTG CCA GGG             413
Arg Arg Ser Leu Ala Gln Asp Ala Pro Pro Leu Pro Val Pro Gly
                110                 115                 120

GTG CTT CTG AAG GAG TTC ACT GTG TCC GGC AAC ATA CTG ACT ATC             458
Val Leu Leu Lys Glu Phe Thr Val Ser Gly Asn Ile Leu Thr Ile
                125                 130                 135

CGA CTG ACT GCT GCA GAC CAC CGC CAA CTG CAG CTC TCC ATC AGC             503
Arg Leu Thr Ala Ala Asp His Arg Gln Leu Gln Leu Ser Ile Ser
                140                 145                 150

TCC TGT CTC CAG CAG CTT TCC CTG TTG ATG TGG ATC ACG CAG TGC             548
Ser Cys Leu Gln Gln Leu Ser Leu Leu Met Trp Ile Thr Gln Cys
                155                 160                 165

TTT CTG CCC GTG TTT TTG GCT CAG CCT CCC TCA GGG CAG AGG CGC             593
Phe Leu Pro Val Phe Leu Ala Gln Pro Pro Ser Gly Gln Arg Arg
                170                 175                 180

TAAGCCCAGC CTGGCGCCCC TTCCTAGGTC ATGCCTCCTC CCCTAGGGAA                  643

TGGTCCCAGC ACGAGTGGCC AGTTCATTGT GGGGGCCTGA TTGTTTGTCG                  693

CTGGAGGAGG ACGGCTTACA TGTTTGTTTC TGTAGAAAAT AAAACTGAGC                  743

TACGAAAAA                                                               752

(2) INFORMATION FOR SEQ ID NO: 2:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO: 2:

CACACAGGAT CCATGGATGC TGCAGATGCG G                                       31

(2) INFORMATION FOR SEQ ID NO: 3:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO: 3:

CACACAAAGC TTGGCTTAGC GCCTCTGCCC TG                                      32

(2) INFORMATION FOR SEQ ID NO: 4:
```

```
        (i) SEQUENCE CHARACTERISTICS:
            (A) LENGTH: 11 amino acids
            (B) TYPE: amino acid
            (D) TOPOLOGY: linear (xi) SEQUENCE DESCRIPTION: SEQ ID NO: 4:

Ser Leu Leu Met Trp Ile Thr Gln Cys Phe Leu
                 5                  10

(2) INFORMATION FOR SEQ ID NO: 5:

(i) SEQUENCE CHARACTERISTICS:
            (A) LENGTH: 9 amino acids
            (B) TYPE: amino acid
            (D) TOPOLOGY: linear (xi) SEQUENCE DESCRIPTION: SEQ ID NO: 5:

Ser Leu Leu Met Trp Ile Thr Gln Cys
                 5

(2) INFORMATION FOR SEQ ID NO: 6:

(i) SEQUENCE CHARACTERISTICS:
            (A) LENGTH: 9 amino acids
            (B) TYPE: amino acid
            (D) TOPOLOGY: linear (xi) SEQUENCE DESCRIPTION: SEQ ID NO: 6:

Gln Leu Ser Leu Leu Met Trp Ile Thr
                 5

(2) INFORMATION FOR SEQ ID NO: 7:

(i) SEQUENCE CHARACTERISTICS:
            (A) LENGTH: 10 amino acids
            (B) TYPE: amino acid
            (D) TOPOLOGY: linear (xi) SEQUENCE DESCRIPTION: SEQ ID NO: 7:

Leu Leu Met Trp Ile Thr Gln Cys Phe Leu
                 5                  10

(2) INFORMATION FOR SEQ ID NO: 8:

(i) SEQUENCE CHARACTERISTICS:
            (A) LENGTH: 18 amino acids
            (B) TYPE: amino acid
            (D) TOPOLOGY: linear (xi) SEQUENCE DESCRIPTION: SEQ ID NO: 8:

Ala Ala Asp His Arg Gln Leu Gln Leu Ser Ile Ser Ser Cys Leu Gln
                 5                  10                  15

Gln Leu (2) INFORMATION FOR SEQ ID NO: 9:

(i) SEQUENCE CHARACTERISTICS:
            (A) LENGTH: 18 amino acids
            (B) TYPE: amino acid
            (D) TOPOLOGY: linear (xi) SEQUENCE DESCRIPTION: SEQ ID NO: 9:

Val Leu Leu Lys Glu Phe Thr Val Ser Gly Asn Ile Leu Thr Ile Arg
                 5                  10                  15

Leu Thr
```

-continued (2) INFORMATION FOR SEQ ID NO: 10:

(i) SEQUENCE CHARACTERISTICS:
        (A) LENGTH: 18 amino acids
        (B) TYPE: amino acid
        (D) TOPOLOGY: linear (xi) SEQUENCE DESCRIPTION: SEQ ID NO: 10:

Pro Leu Pro Val Pro Gly Val Leu Leu Lys Glu Phe Thr Val Ser Gly
              5                  10               15

Asn Ile (2) INFORMATION FOR SEQ ID NO: 11:

(i) SEQUENCE CHARACTERISTICS:
        (A) LENGTH: 18 amino acids
        (B) TYPE: amino acid
        (D) TOPOLOGY: linear (xi) SEQUENCE DESCRIPTION: SEQ ID NO: 11:

Gly Ala Ala Ser Gly Leu Asn Gly Cys Cys Arg Cys Gly Ala Arg Gly
              5                  10               15

Pro Glu (2) INFORMATION FOR SEQ ID NO: 12:

(i) SEQUENCE CHARACTERISTICS:
        (A) LENGTH: 18 amino acids
        (B) TYPE: amino acid
        (D) TOPOLOGY: linear (xi) SEQUENCE DESCRIPTION: SEQ ID NO: 12:

Ser Arg Leu Leu Glu Phe Tyr Leu Ala Met Pro Phe Ala Thr Pro Met
              5                  10               15

Glu Ala (2) INFORMATION FOR SEQ ID NO: 13:

(i) SEQUENCE CHARACTERISTICS:
        (A) LENGTH: 18 amino acids
        (B) TYPE: amino acid
        (D) TOPOLOGY: linear (xi) SEQUENCE DESCRIPTION: SEQ ID NO: 13:

Thr Val Ser Gly Asn Ile Leu Thr Ile Arg Leu Thr Ala Ala Asp His
              5                  10               15

Arg Gln (2) INFORMATION FOR SEQ ID NO: 14:

(i) SEQUENCE CHARACTERISTICS:
        (A) LENGTH: 6 amino acids
        (B) TYPE: amino acid
        (D) TOPOLOGY: linear (xi) SEQUENCE DESCRIPTION: SEQ ID NO: 14:

Leu Leu Met Trp Ile Thr
              5

(2) INFORMATION FOR SEQ ID NO: 15:

(i) SEQUENCE CHARACTERISTICS:
        (A) LENGTH: 180 amino acids

```
        (B) TYPE: amino acid
        (D) TOPOLOGY: linear (xi) SEQUENCE DESCRIPTION: SEQ ID NO: 15

Met Gln Ala Glu Gly Arg Gly Thr Gly Gly Ser Thr Gly Asp Ala
                 5                  10                  15

Asp Gly Pro Gly Gly Pro Gly Ile Pro Asp Gly Pro Gly Gly Asn
                20                  25                  30

Ala Gly Gly Pro Gly Glu Ala Gly Ala Thr Gly Gly Arg Gly Pro
                35                  40                  45

Arg Gly Ala Gly Ala Arg Ala Ser Gly Pro Gly Gly Gly Ala
                50                  55                  60

Pro Arg Gly Pro His Gly Gly Ala Ala Ser Gly Leu Asn Gly Cys
                65                  70                  75

Cys Arg Cys Gly Ala Arg Gly Pro Glu Ser Arg Leu Leu Glu Phe
                80                  85                  90

Tyr Leu Ala Met Pro Phe Ala Thr Pro Met Glu Ala Glu Leu Ala
                95                 100                 105

Arg Arg Ser Leu Ala Gln Asp Ala Pro Pro Leu Pro Val Pro Gly
               110                 115                 120

Val Leu Leu Lys Glu Phe Thr Val Ser Gly Asn Ile Leu Thr Ile
               125                 130                 135

Arg Leu Thr Ala Ala Asp His Arg Gln Leu Gln Leu Ser Ile Ser
               140                 145                 150

Ser Cys Leu Gln Gln Leu Ser Leu Leu Met Trp Ile Thr Gln Cys
               155                 160                 165

Phe Leu Pro Val Phe Leu Ala Gln Pro Pro Ser Gly Gln Arg Arg
               170                 175                 180
```